(12) United States Patent
Machida et al.

(10) Patent No.: US 6,284,119 B1
(45) Date of Patent: Sep. 4, 2001

(54) DNA BASE SEQUENCER

(75) Inventors: Hiroaki Machida; Yusuke Miyazaki, both of Saitama-ken; Mitsuyoshi Koizumi, Yokohama, all of (JP)

(73) Assignee: Hitachi Electronics Engineering Co., Ltd., Tokyo (JP)

( * ) Notice: Subject to any disclaimer, the term of this patent is extended or adjusted under 35 U.S.C. 154(b) by 0 days.

(21) Appl. No.: 09/385,025

(22) Filed: Aug. 30, 1999

(30) Foreign Application Priority Data

Aug. 31, 1998 (JP) .................................................. 10-245341
Aug. 31, 1998 (JP) .................................................. 10-245342
Aug. 31, 1998 (JP) .................................................. 10-245343

(51) Int. Cl.[7] .................................................. G01N 27/26
(52) U.S. Cl. .................................................. 204/612; 356/344
(58) Field of Search .................................................. 204/452, 461, 204/603, 612; 356/344; 382/128, 129

(56) References Cited

FOREIGN PATENT DOCUMENTS

| 63-21556 | 1/1988 | (JP) . |
|---|---|---|
| 5-72177 | 3/1993 | (JP) . |
| 10-132784 | 5/1998 | (JP) . |

*Primary Examiner*—Jill Warden
*Assistant Examiner*—Alb Nogueroln
(74) *Attorney, Agent, or Firm*—Mattingly, Stanger & Malur, P.C.

(57) ABSTRACT

A DNA base sequencer including a gel electrophoretic means having tracks for electrophoresing fluorophore-labelled DNA fragments, a laser diode as a light source for illuminating said tracks with exciting laser light and a CCD sensor for detecting the fluorescence emitted from the illuminated DNA fragments, the laser diode has a control unit including a Peltier device for controlling the temperature of the laser diode, a Peltier device temperature setting generating means having a processor and a memory, and a temperature control circuit that generates a drive current to the Peltier device for controlling its temperature. The CCD sensor receives part of the exciting light from the laser diode as stray light and detects its wavelength. The Peltier device temperature setting generating means is such that, in accordance with the wavelength of stray light as detected periodically with said CCD sensor according to the program stored in said memory, it calculates a corrective value that adjusts the detected wavelength of stray light to the desired wavelength of exciting light that corresponds to the desired temperature setting and that an appropriate temperature setting signal is generated on the basis of said corrective value and the desired temperature setting and sent to the Peltier device temperature control circuit.

12 Claims, 8 Drawing Sheets

DNA BASE SEQUENCER

BACKGROUND OF INVENTION

This invention relates to a DNA base sequencer, or an apparatus for determining the base sequences of DNA. More particularly, this invention relates to an apparatus with which the base sequences of DNA can be determined by fluorescent labelling in an efficient and rapid manner.

Gel electrophoresis is practiced extensively as a technique for determining the base sequences of DNA and other proteins.

Conventionally, the sample to be subjected to electrophoresis is labelled with a radioisotope for analysis but this method has had the problem of being painstaking and time-consuming. Furthermore, the use of radioactive substances always calls for utmost safety and management and analysis cannot be performed in areas other than facilities that clear certain regulations. Under the circumstances, a method that uses fluorophores to label the sample and which detects fluorescence as emitted upon irradiation with light is being reviewed.

In this method, fluorophore-labelled DNA fragments are caused to migrate through a gel and a light excitation portion and a photodetector are provided for each electrophoresis track in an area 15–20 cm below the start point of electrophoresis. The DNA fragments are assayed as they pass through the line connecting the light excitation portion and the photodetector. A typical procedure of the method is described below. First, using as template the DNA chain to be determined for its base sequence, DNAs of various lengths with known terminal base species are replicated by a method involving an enzymatic reaction (the dideoxy method). Then, the replicated DNAs are labelled with a fluorophore. Stated more specifically, there are prepared a group of adenine (A) fragments, a group of cytosine (C) fragments, a group of guanine (G) fragments and a group of thymine (T) fragments, all being labelled with a fluorophore. A mixture of these fragment groups is injected into separate lane grooves in an electrophoretic gel and, thereafter, a voltage is applied at opposite ends of the gel. Since DNA is a chained polymer with negative charges, it will move across the gel at a rate in inverse proportion to its molecular weight. The shorter the DNA chain (the smaller its molecular weight), the faster will it move and vice versa; this is the principle behind the fractionation of DNA by molecular weight.

Japanese Laid-Open Patent Application (kokai) No. 21556/1988, incorporated herein by reference, teaches a DNA base sequencer that is adapted in such a way that a line on the gel in an apparatus for electrophoresis at which laser light is applied and the direction in which photodiodes are arranged are both perpendicular to the direction in which DNA fragments migrate in the apparatus.

The setup of this apparatus is shown schematically in FIG. 11. In the apparatus shown in FIG. 11, a laser beam emitted from a light source 70 is reflected by a mirror 72 and launched horizontally from one side of the plate 74 at a predetermined point on the gel. As the fluorophore-labelled DNA fragments migrating through the gel pass through the irradiated region, they will fluoresce successively. The horizontal position of fluorescence emission tells the species of a particular terminal base, the time difference from the start of migration tells the length of a particular fragment, and the emission wavelength identifies the sample under assay. The fluorescence from each electrophoresis track is condensed by a lens 78 to focus at a light-receiving area 82 in an image intensifier 80. The received signal is amplified and converted to an electric signal in a photodiode array 84 for the purpose of various measurements. The results of measurements are processed with a computer so that the sequences of the individual DNA fragments are calculated to determine the base sequence of the DNA at issue.

The apparatus shown in FIG. 11 uses an image intensifier camera in the light-receiving optics. The image intensifier camera is not only very expensive but also comparatively large as an optical device. The overall size of the electrophoretic apparatus becomes inevitably bulky.

The light source is a gas laser using Ar or He—Ne as a lasing medium. These laser light sources are usually very expensive. The DNA sequencer of the type that has exciting light applied to the gel layer from one lateral side has the following problems: (1) the beam of exciting laser light cannot be focused to a sufficiently small diameter over a long range so that the spatial resolution is limited; (2) in order to solve this problem, the beam was spread to an elliptical form in the direction of electrophoresis so that the spatial resolution could be improved in the pixels of the sensor; however, most of the beams emitted from gas lasers have a circular cross-sectional profile and complicated illumination optics is required to spread the beam to an elliptical form.

To solve these problems, the present inventors previously invented a DNA base sequencer using a CCD line sensor as light-receiving optics and a laser diode (hereunder LD) as an exciting light source. This apparatus was applied for patent and is now described in Japanese Laid-Open Patent Application (kokai) No. 132784/1998, incorporated herein by reference. The exciting light emitted by LD has a beam divergence angle of 7.5×37 degrees. As is apparent from this characteristic value, the laser diode emits a generally elliptical beam. Therefore, unlike a gas laser which emits a beam having a circular cross section, the laser diode does not require any special optics to produce an elliptical beam. Compared to the image intensifier camera, the CCD line sensor is not only very compact but also inexpensive. Similarly, compared to the gas lasers, the LD is not only compact but also very cheap. Therefore, as a result of using the CCD line sensor as light-receiving optics and the LD as an exciting light source, not only the overall size but also the cost of the DNA base sequencer could be dramatically reduced.

However, continued studies of the present inventors have revealed that the oscillation wavelength of LD is instable, making it fairly difficult to obtain a specified wavelength in a consistent manner. As it turned out, LD has the following features: (1) if the optical output is fixed, the forward current increases with increasing temperature; (2) if the temperature of the casing increases, the oscillation wavelength also increases, typically at a rate of 0.23 nm/° C. Under the circumstances, the present inventors made an attempt at holding the oscillation wavelength of LD constant by controlling its temperature with the aid of a Peltier device. The oscillation wavelength of LD also varies with the drive current. To deal with this problem, the present inventors combined LD with a photodiode, detected the current through the photodiode and attempted to keep the LD drive current constant on the basis of the detected current value by means of an automatic power control (APC) device connected to the LD.

In this approach, the LD current and temperature are monitored and one can only presume indirectly that the oscillation wavelength of LD should be constant if the monitored values remain the same. The variations in the oscillation wavelength are not detected. Therefore, even if the temperature of LD casing is controlled to remain constant at 20° C. with the aid of a Peltier device in order to keep the oscillation wavelength of LD at 637 nm, a shift to the longer wavelength side may occur during ID operation. If the operator continues DNA analysis without becoming aware of this event, the data obtained is not completely reliable. If part of the exciting light in the longer wavelength range is received by a fluorescence detector as stray light, it overlaps the fluorescence at a nearby wavelength (say, 650 nm), making it difficult or even impossible to locate or separate the fluorescence that should be detected.

Other studies made on the apparatus shown in FIG. 11 and the apparatus disclosed in Japanese Laid-Open Patent Application No. 132784/1998, supra have revealed the following problems with the use of flat electrophoresis plate: (1) it takes considerable time to inject a fluorophore-labelled DNA sample into all electrophoresis tracks; (2) contamination often occurs due to sample mixing in adjacent electrophoresis tracks; (3) the DNA sample may depart from the correct track to either right or left during electrophoresis and this phenomenon, commonly called "smiling", can cause errors in measurement.

Under the circumstances, a DNA base sequencer was developed that used a hollow capillary, rather than the flat plate, as electrophoretic means. The capillary is filled with a gel electrolyte and a fluorophore-labelled DNA sample is injected into the capillary from one open end; thereafter, the other open end of the capillary is immersed in a buffer tank serving as a negative electrode and the open end from which the DNA sample was injected is immersed in a buffer tank serving as a positive electrode; when a voltage of −15 kV is applied, the DNA fragments are electrophoresed. The apparatus having this construction is disclosed in Japanese Laid-Open Patent Application (kokai) No. 72177/1993, incorporated herein by reference. Specifically, a gas laser is used as an exciting light source and a plurality of capillaries are aligned on a longitudinal axis such that the exciting light travels from one end of the line to the other, The present inventors made an experiment using as a light source the laser diode of Japanese Laid-Open Patent Application (kokai) No. 132784/1998, supra, instead of the gas laser of Japanese Laid-Open Patent Application (kokai) No. 72177/1993, supra. As it turned out, incident laser light was extensively scattered by the first capillary and the scattered laser light became stray light that was another source of errors in measurement.

SUMMARY OF INVENTION

An object, therefore, of the present invention is to provide a DNA base sequencer having a novel mechanism for maintaining the oscillation wavelength of LD constant.

Another object of the invention is to provide a DNA base sequencer having a novel mechanism for ensuring that the exciting laser light emitted from LD has a constant wavelength.

A further object of the invention is to provide a DNA base sequencer that uses a capillary as electrophoretic means and a laser diode as an exciting light source while permitting limited scattering of the laser light.

The first object of the invention can generally be attained by a system in which part of the exciting light transmitted through a long-pass filter used in fluorescence-receiving optics is received by a CCD sensor, the wavelength of the exciting light is monitored and the result is fed back to control the drive of a Peltier device. An example of this system is a DNA base sequencer comprising a gel electrophoretic means having tracks for electrophoresing fluorophore-labelled DNA fragments, a laser diode as a light source for illuminating said tracks with exciting laser light and a CCD sensor for detecting the fluorescence emitted from the illuminated DNA fragments, wherein said laser diode has a control unit comprising a Peltier device for controlling the temperature of the laser diode, a Peltier device temperature setting generating means having a processor and a memory, and a temperature control circuit that generates a drive current to the Peltier device for controlling its temperature, further characterized in that said CCD sensor receives part of the exciting light from the laser diode as stray light and detects its wavelength and that said Peltier device temperature setting generating means is such that, in accordance with the wavelength of stray light as detected periodically with said CCD sensor according to the program stored in said memory, calculates a corrective value that adjusts the detected wavelength of stray light to the desired wavelength of exciting light that corresponds to the desired temperature setting and that an appropriate temperature setting signal is generated on the basis of said corrective value and said desired temperature setting and sent to the Peltier device temperature control circuit, whereby the oscillation wavelength of the LD is maintained constant.

The second object of the invention can be attained by providing a short-pass filter between the laser diode and the gel electrophoretic means on their optical axis so as to transmit only the exciting light having a desired wavelength.

The third object of the invention can be attained by using a single hollow capillary as the gel electrophoretic means and providing the laser diode in such a position that laser light is launched at an incident angle greater than zero degrees but smaller than 90 degrees, preferably from 30 degrees to 60 degrees, most preferably at 45 degrees, with respect to the normal to the capillary.

EMBODIMENTS OF THE INVENTION

Figure 1:
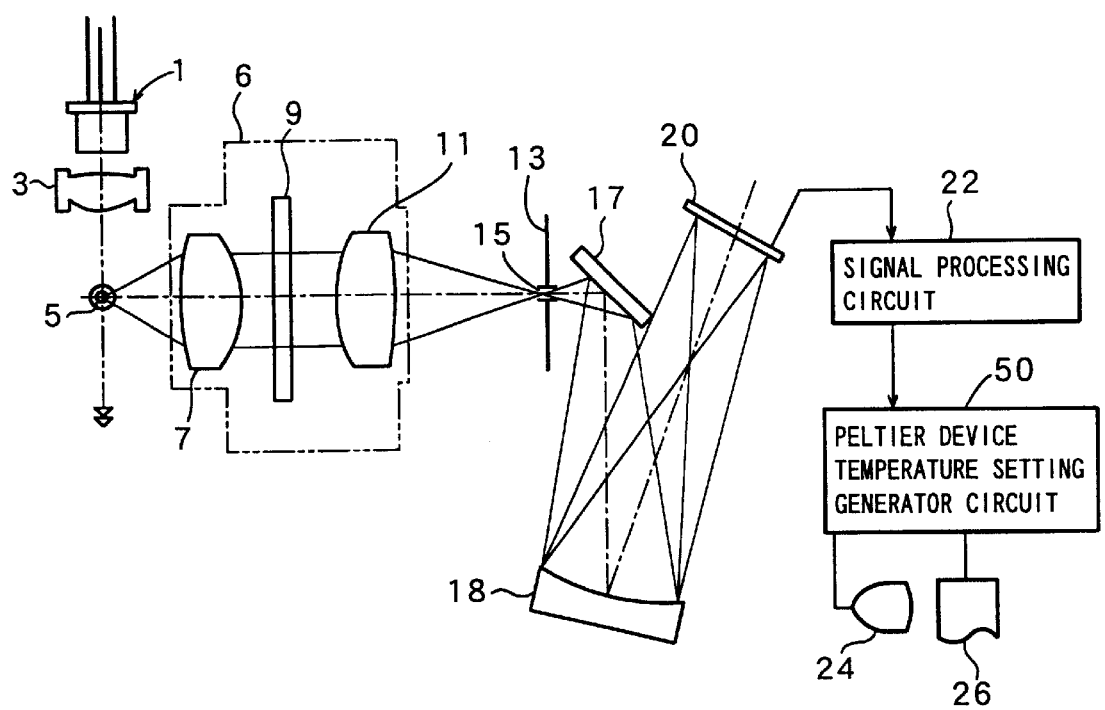
FIG. 1 shows grammatically a partial layout of the DNA base sequencer of the invention.

FIG. 1 shows grammatically a partial layout of the DNA base sequencer of the invention. As shown, the DNA base sequencer of the invention uses LD 1 in place of a gas laser as a source of exciting light. An example of the LD that can be used in the invention is commercially available from Hitachi, Ltd. under the trade name HL 6319G. This LD has an emission wavelength of 637 nm and can produce a power of 7 mW. The exciting light it emits has a beam divergence angle of 7.5×37 degrees. As is apparent from this characteristic value, the LD emits a generally elliptical beam. Therefore, unlike a gas laser which emits a beam having a circular cross section, the LD does not require any special optics to produce an elliptical beam. Laser diodes having specifications other than those set forth above may of course be used in the apparatus of the invention.

The exciting light emitted from LD 1 passes through a condenser lens 3 to be focused in a specified position on an electrophoretic means 5. The electrophoretic means 5 shown in FIG. 1 is a single hollow capillary but this may be replaced by a plurality of hollow capillaries or the conventional flat electrophoretic plate. When a sample of fluorophore-labeled DNA fragments within the electrophoretic means 5 is illuminated with the exciting light, the fluorophore emits fluorescence at a specified wavelength. Exemplary fluorescence labels for DNA fragments include FITC (fluorescein isothiocyanate), EITC (eosin isothiocyanate), TMRITC (tetramethyl rhodamine isothiocyanate) and XRITC (substituted rhodamine isothiocyanate). Other fluorescence labels may of course be used.

The fluorescence emitted from the fluorescence label is collected with fluorescence collecting optics 6. It is first collected with a first lens 7, collimated and passed through a long-pass filter 9. The long-pass filter 9 transmits fluorescence having wavelengths longer than 650 nm but rejects stray light at shorter wavelengths that is incident together with the fluorescence (as exemplified by scattered exciting light having a wavelength of 637 nm). In practice, however, the long-pass filter 9 is not capable of complete rejection of the exciting light having a wavelength of 637 nm. Filters are available that can reject nearly 100% of such exciting light but since they are very expensive and increase the overall cost of the apparatus, they are seldom used. Commonly used long-pass filters have exciting light transmittances of from about 0.05% to about 0.07% and they are available at fairly low cost. The long-pass filter 9 is one of these inexpensive versions but part of the transmitted exciting light is included as stray light in the fluorescence.

The fluorescence and an extremely small amount of stray light that have been transmitted through the long-pass filter 9 are re-focused with a second lens 11, typically at a point generally coinciding with the center of a slit 15 in a plate 13. The re-focused fluorescence (including the stray light) is reflected by a mirror 17 to be incident on a grating 18, from which it is reflected again to be launched into a CCD sensor 20. The grating 18 used in the apparatus shown in FIG. 1 is an optical member that uses the diffraction of light to produce a spectrum, select a particular wavelength or polarize the light. The grating 18 has a periodic pattern of asperities formed on a flat or concave substrate. Any of the diffraction gratings having other structures may be used as the grating 18. The CCD sensor 20 is known in the art. The CCD sensor 20 that may be used in the apparatus of the invention is typically of 512×64 pixels. During its operation, the CCD sensor 20 is typically cooled to −10° C. by a known conventional means such as a Peltier device.

The fluorescence and stray light that have been detected with the CCD sensor 20 are sent to a signal processing circuit 22, where their wavelengths are detected in correspondence with pixel position and subjected to A/D conversion and other known signal processing steps. Signals representing the obtained pixel position based data are sent to a Peltier device temperature setting circuit 50 which is described later in detail. A CRT 24 of a common PC and/or a printer 26 may be connected to the Peltier device temperature setting circuit 50 so that any necessary data can be output by these output means.

Figure 2:
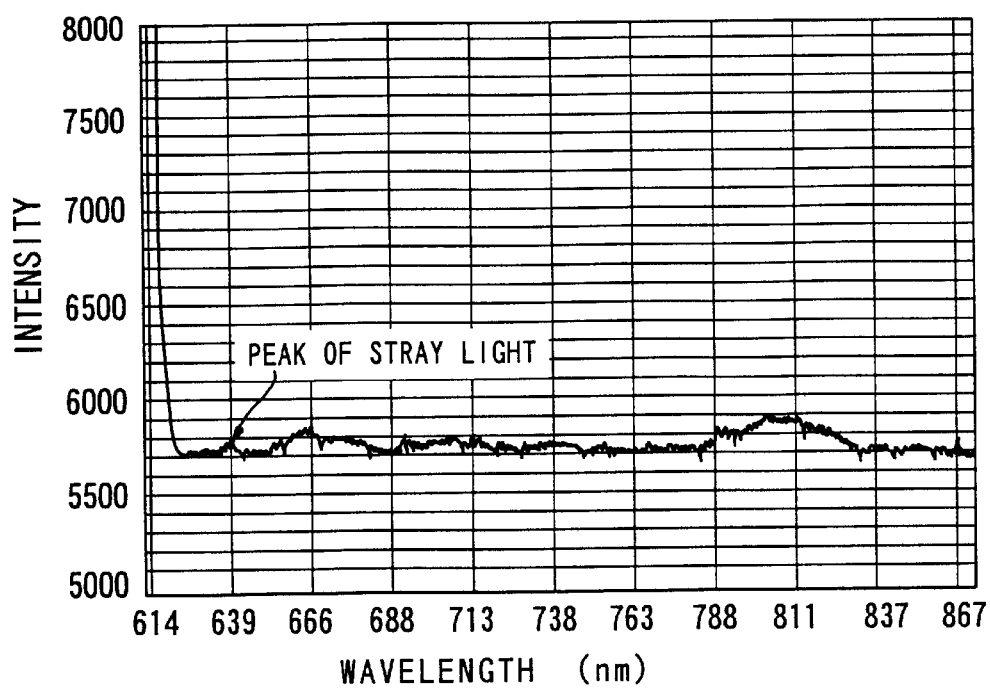
FIG. 2 is a characteristic diagram showing exemplary data on the Raman scattering with the apparatus shown in FIG. 1.

FIG. 2 is a characteristic diagram showing exemplary data on the Raman scattering with the apparatus shown in FIG. 1. As mentioned above, the long-pass filter 9 used in the apparatus of the invention which is shown in FIG. 1 is not capable of complete rejection of the exciting light being incident as stray light. The stray light transmitted through this long-pass filter 9 is eventually received and detected by the CCD sensor 20. FIG. 2 shows the detection of a weak peak near 639 nm, which corresponds to the peak of stray light (from the exciting light). Since the design wavelength of the exciting light is 637 nm, the peak wavelength of the stray light has a 2 nm shift to the longer side. As is generally known, CCD pixels substantially correlate to wavelength in terms of position. Therefore, it is preferred to use the CCD sensor 20 after confirming the positional relationship between a particular CCD pixel and the wavelength of 637 nm. A generally valid relationship is 0.5 nm/pixel although this is not intended to limit the scope of the invention. The data on Raman scattering shown in FIG. 2 may be displayed on a real time basis on the monitor screen 24 of a PC.

The peak shift of the stray light (from the exciting light) to the longer wavelength side is generally due to the increase in the temperature of LD. To give a few, non-limiting examples, the wavelength which is 637 nm at 20° C. increases to about 638 nm at 25° C. and about 639 nm at 30° C. If stray light having a wavelength of 639 nm and fluorescence having a wavelength of 650 nm both exist, they are extremely difficult to separate. Therefore, in the case of a DNA base sequencer using LD as an exciting light source, at least the exciting light at 637 nm must be sharply separated from the fluorescence at 650 nm.

Figure 3:
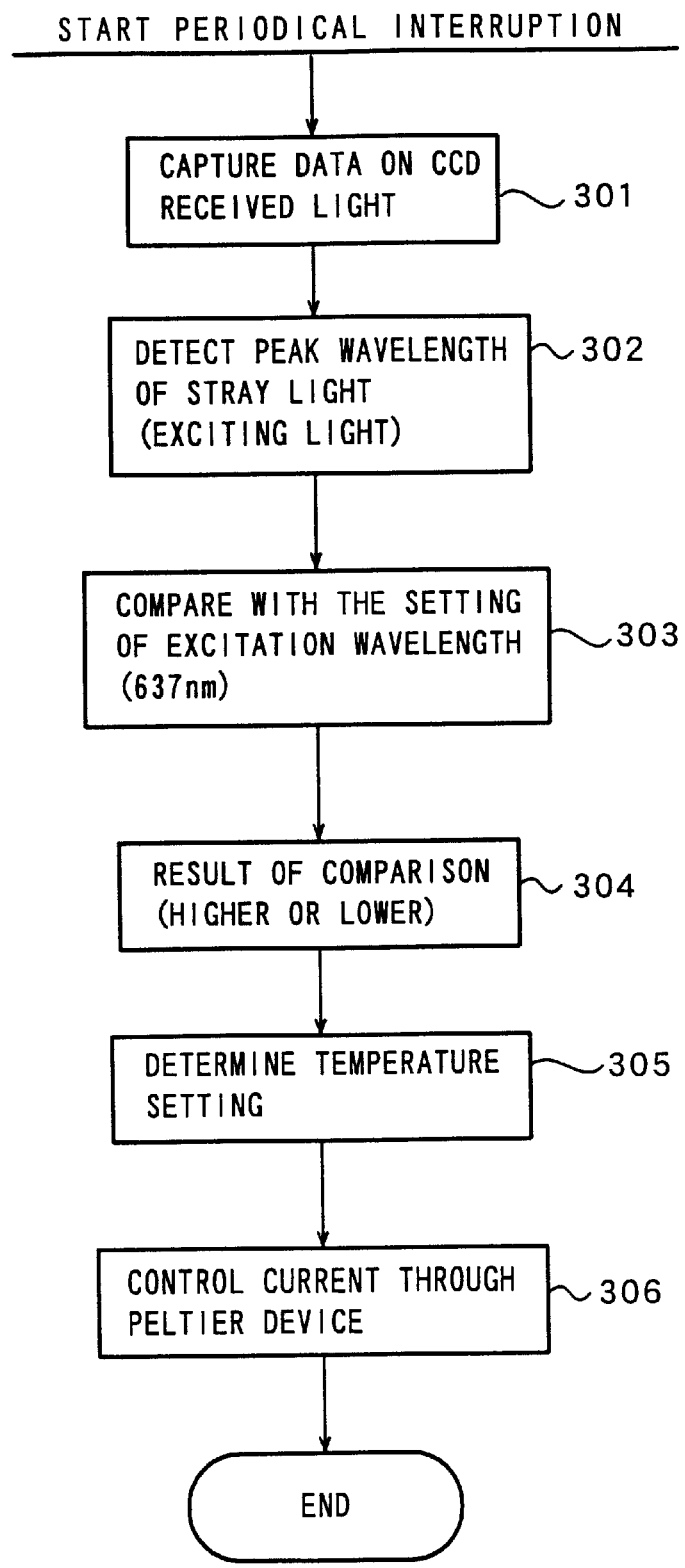
FIG. 3 is a flowchart for the sequence of steps in the process of controlling the current through an LD cooling Peltier device using the stray light detected with CCD.

FIG. 3 is a flowchart for the sequence of steps in the process of controlling the current through an LD cooling Peltier device using the stray light detected with CCD. A forward current is flowed through the Peltier device to cool the casing of LD and a reverse current is applied to heat it. As shown, the data on light reception by CCD is captured periodically (step 301). Then, the peak of the stray light (exciting light) output as detected with the CCD 20 is detected (step 302). This peak is determined in terms of wavelength and expressed as, for example, 638 nm or 639 nm. In step 303, the determined peak is compared with the specified setting (i.e., 637 nm). In step 304, the difference from the specified setting is calculated as a numerical value by which the determined value is "higher" or "lower" than the specified setting. In step 305, specified arithmetic operations are performed on the basis of the result of calculation of the difference in step 304 to set the temperature of LD. A generally valid relationship is 0.23 nm/° C. but since this varies from one LD to another, it is preferred to operate a specific LD after confirming its temperature-wavelength relationship by experiment. On the basis of the temperature setting determined in step 305, the current being flowed through the Peltier device is controlled in step 306. For example, if the wavelength of stray light is found to have shifted to the longer side, a forward current is applied to the Peltier device so that the LD is cooled by a sufficient temperature to compensate for the shift. As a result, the wavelength of the stray light detected with CCD decreases to a value nearest to 637 nm which is the design value that should be observed by the stray light. When the value of 637 nm is reached, the supply of a forward current to the Peltier device is stopped. On the other hand, if the wavelength of the stray light is found to have shifted to the shorter side, a reverse current is applied to the Peltier device, whereupon the temperature of LD increases and the wavelength of the stray light becomes the nearest to 637 nm. In this way, the wavelength of the stray light as received by the CCD is detected at all times and, on the basis of the result, the Peltier device is controlled on a real-time basis such that the wavelength of the exciting light is maintained at 637 nm throughout the operation of the apparatus.

The conventional DNA base sequencer using LD as a source of exciting light has been operated on the premise that if only the LD is maintained at 20° C. by means of a Peltier device, the excitation wavelength should also be held at 637 nm. Since no check has been made to confirm that the excitation wavelength of LD is actually 637 nm at 20° C., any departure from 637 nm has been impossible to correct effectively. In the present invention, LD is cooled while the excitation wavelength is actually monitored, so the departure from 637 nm is almost absent and the resolution in separating the stray light from fluorescence having a wavelength of 650 nm is dramatically improved.

The process consisting of monitoring the wavelength of the stray light as detected with CCD and controlling the Peltier device to adjust the temperature of LD may be performed either independently or in combination with the conventional method of controlling the temperature of LD casing with the aid of a Peltier device and performing APC control to maintain the current through LD constant.

Figure 4:
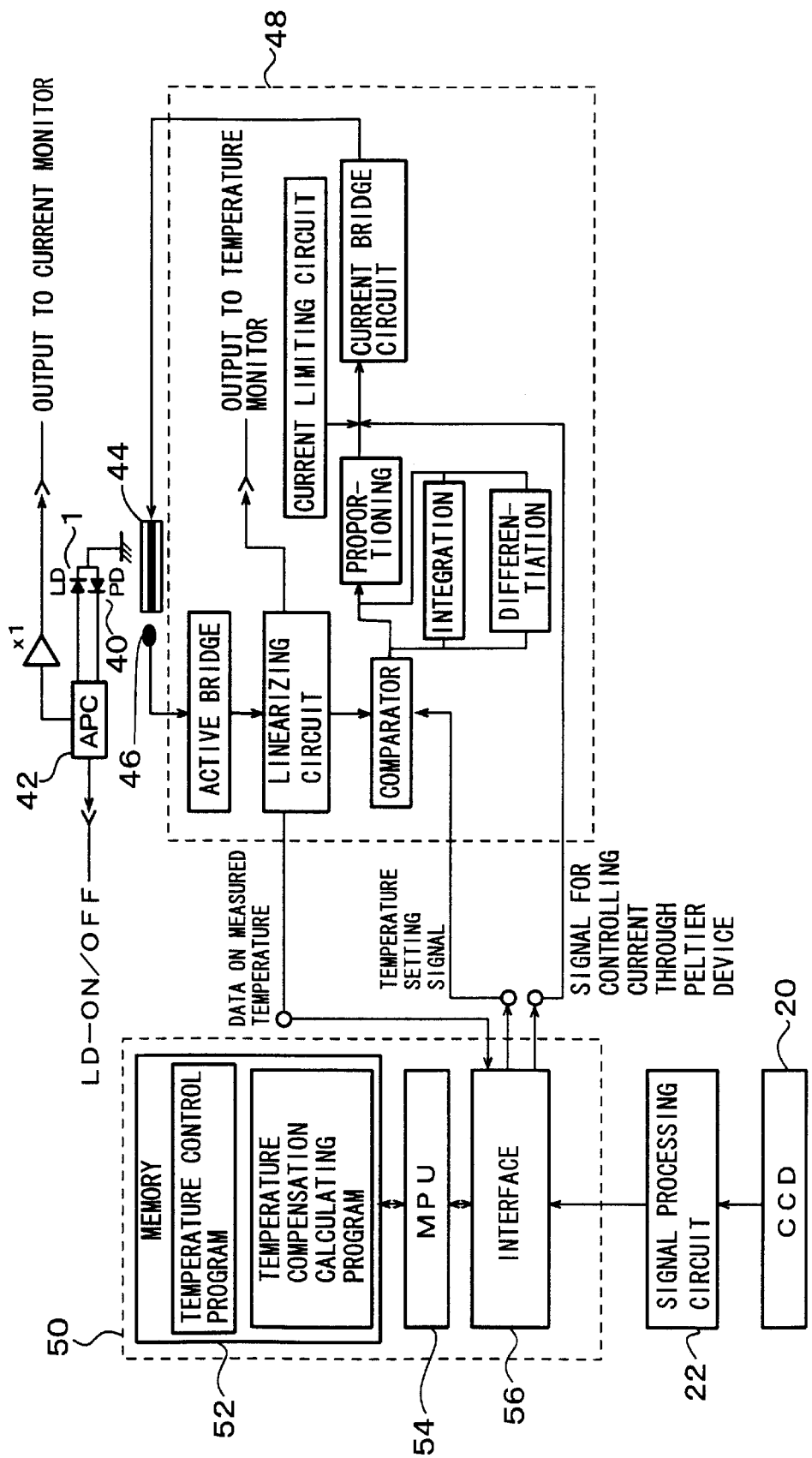
FIG. 4 is a block diagram for an exemplary mechanism for maintaining the oscillation wavelength of LD constant.

FIG. 4 is a block diagram for an exemplary mechanism for maintaining the oscillation wavelength of LD constant. In FIG. 4, the mechanism for feeding back the detected wavelength of stray light according to the present invention is combined with two conventional mechanisms, one for maintaining a constant current through LD and the other for maintaining a constant temperature for the casing of LD. As shown, LD 1 forms a closed circuit with a photodiode (PD) 40 and is connected to an automatic power control (APC) circuit 42. Both LD 1 and PD 40 are grounded. The Peltier device indicated by 44 is provided adjacent to LD 1. The temperature of the casing of LD 1 is detected with a suitable temperature detecting means 46 (e.g., a thermistor). The result of detection with the temperature detecting means 46 is first sent to a Peltier device temperature control circuit 48. If desired, it may be linearized and output to a temperature monitor.

The Peltier device temperature setting circuit 50 shown in FIG. 4 has a memory 52 loaded with a Peltier device temperature controlling program and a temperature corrective value calculating program, a processor (MPU) 54 for executing the two programs, and an interface 56. The temperature as detected by the temperature detecting means 46 is supplied to a linearizing circuit in the Peltier device temperature control circuit 48, from which it is forwarded to the interface 56. The wavelength of the stray light (exciting light) as received by the CCD 20 is first input to the interface 56, then processed with MPU 54 in cooperation with the memory 52 to produce a temperature setting signal and a signal for controlling the current through the Peltier device; the two signals are output to the Peltier device temperature control circuit 48.

As the current through the Peltier device 44 is controlled, the temperature of LD 1 varies and so does the peak wavelength of the stray light being detected by the CCD 20. At the point of time when said peak wavelength has reached the setting of 637 nm, the Peltier device temperature setting circuit 50 stops acquiring the peak of stray light from the CCD 20. This procedure is repeated periodically to ensure that the wavelength of the exciting light from LD 1 is maintained constant.

The peak of stray light is acquired from the CCD at given intervals. As long as no peak acquisition is performed, the current through the Peltier device 44 may be controlled with reference to a common setting for the temperature of LD (say, 20° C.).

Figure 5:
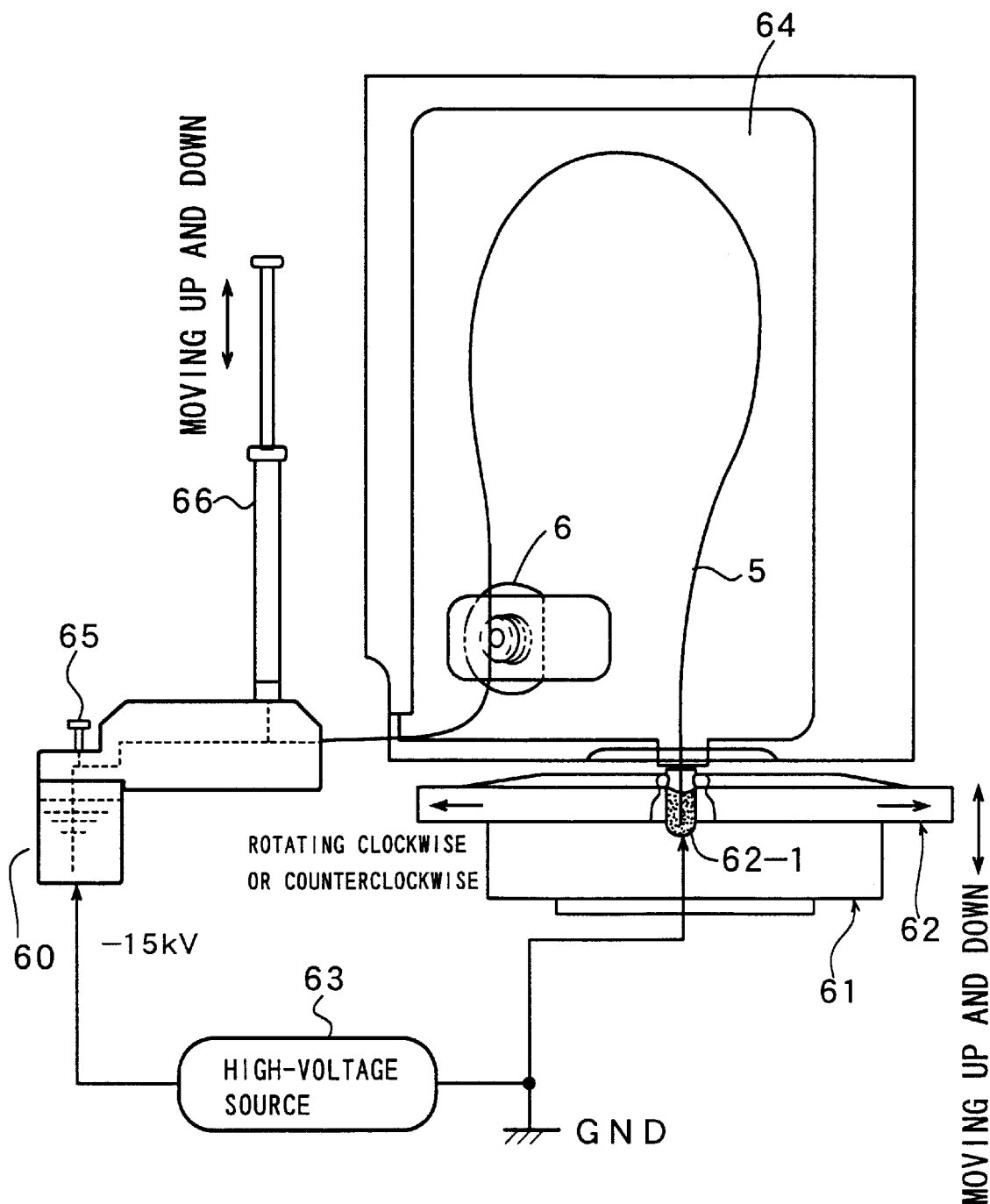
FIG. 5 is a front view showing grammatically, with part taken away, a DNA base sequencer using a single capillary according to the invention.

FIG. 5 is a front view showing schematically, with part taken away, the DNA base sequencer of the invention shown in FIG. 1. One end of a capillary 5 is immersed in a buffer solution in a lower buffer tank 60 and the other end is immersed in a buffer solution in an upper buffer tank 62-1 in a sample tray 62 on a sample feed unit 61. The lower buffer tank 60 and the upper buffer tank 62-1 are supplied with high voltage from a high voltage source 63. Typically, the lower buffer tank 60 is supplied with a negative voltage of −15 kV and the upper buffer tank 62-1 is grounded. To ensure that the temperature of a gel electrolyte in the capillary 5 is held constant throughout electrophoresis, a heater unit 64 is provided as a temperature adjusting means at the back of the capillary 5. The heater unit 64 has a window at a specified site and the fluorescence collecting optics 6 shown in FIG. 1 is provided in a position corresponding to the window. The capillary 5 is positioned in a face-to-face relationship with the fluorescence collecting optics 6 through the window.

Figure 6:
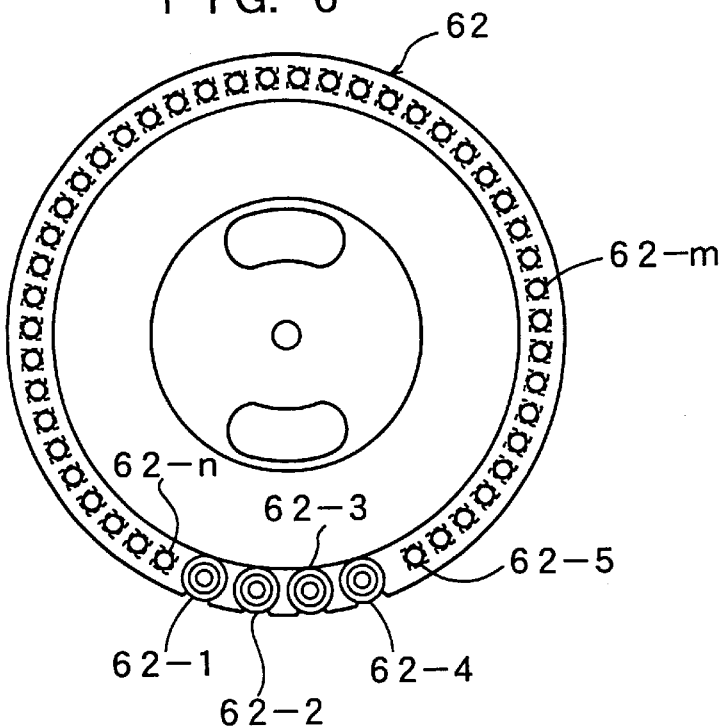
FIG. 6 is a top view of the sample tray used in the apparatus shown in FIG. 5.

FIG. 6 is a top view of the sample tray 62. As shown, the sample tray 62 is disk-shaped and adapted to be rotatable either clockwise or counterclockwise after being mounted on the sample feed unit 61. The sample tray 62 holds the upper buffer tank 62-1, a "garbage boxy" 62-2 into which the gel electrolyte and DNA sample are dumped from the capillary 5 after electrophoresis, a spare-part upper buffer tank 62-3, and a spare-part "garbage box" 62-4. A sample of fluorophore-labeled DNA fragments is placed into each of wells 62-5 to 62-n. The upper buffer tank, "garbage boxes" and the sample of fluorophore-labeled DNA fragments may be used in such a way that plastic tubes extending from them are inserted into each of the wells 62-5 to 62-n.

Referring back to FIG. 5, when gel electrophoresis ends, the sample feed unit 61 comes down so that the capillary 5 is pulled out of the upper buffer tank 62-1. Then, the sample feed unit 61 turns through a specified angle and goes up so that the capillary 5 is inserted into the "garbage box" 62-2. After closing one end of the capillary 5 with a stopper 65, the piston of a gel electrolyte injecting syringe 66 is forced down, whereupon both the gel electrolyte and the sample of DNA fragments are discharged from the other open end of the capillary 5 into the "garbage box" 62-2. The syringe 66 is then filled with a fresh gel electrolyte and the piston is forced down, whereupon the now empty capillary 5 is filled with the fresh gel electrolyte. Thereafter, the sample feed unit 61 comes down so that the capillary 5 is pulled out of the "garbage box" 62-2. Then, the sample feed unit 61 turns through a specified angle and goes up again so that the capillary 5 is inserted into a tube filled with a sample of DNA fragments in a well 62-m in a specified position. When the piston of the syringe 5 is pulled up, the sample of DNA fragments is sucked into the capillary 5. Thereafter, the sample feed unit 61 is lowered and turned to the position of the upper buffer tank 62-1; the sample feed unit 61 is then raised so that the other end of the capillary 5 is inserted into the upper buffer tank 62-1 until it is immersed in the buffer solution in the tank. This completes the process of sample loading. The stopper 65 is released and voltage is applied from the high voltage source 63 to start another run of gel electrophoresis. The sequence of the steps described above may be formulated into a program, which is stored in a suitable memory and executed in a fully automatic way. Various means of automating the steps are known in the art.

Figure 7:
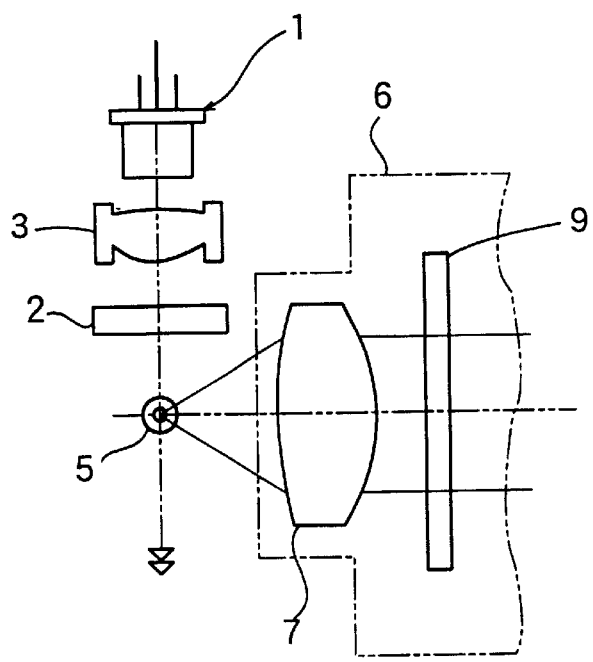
FIG. 7 shows diagrammatically part of a DNA base sequencer having a short-pass filter provided between LD light source 1 and gel electrophoretic means 5.

FIG. 7 shows another embodiment of the invention, in which a short-pass filter 2 is provided between the condenser lens 3 and the electrophoretic means 5. The short-pass filter 2 may be provided in another suitable position such as between LD 1 and the condenser lens 3. Ideally, the short-pass filter 2 transmits that portion of the exciting laser light from LD 1 which has the desired wavelength of 637 nm while rejecting longer wavelengths. In practice, the short-pass filter 2 transmits at least 90% of the exciting light having the desired wavelength of 637 nm while transmitting only about 0.01% of the longer wavelengths.

As a result of their extensive studies, the present inventors have found that commercial grades of LD emit not only exciting light having a wavelength of 637 nm but also exciting light having various other wavelengths. If exciting light having wavelengths longer than 637 nm (say, 650 nm) is detected as stray light, it cannot be effectively separated from the fluorescence having a wavelength of 650 nm, potentially causing an error in measurement. It is therefore preferred to use the short-pass filter 2 so that only the exciting light having a wavelength of 637 nm or below is transmitted while rejecting longer wavelengths.

Figure 8:
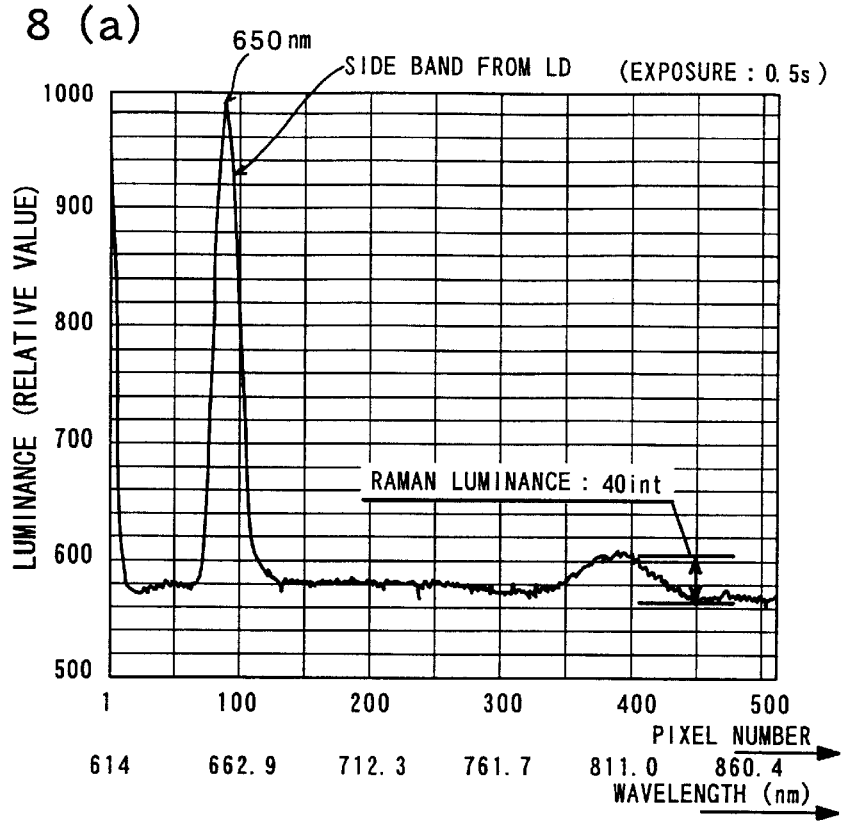
FIG. 8a is a characteristic diagram showing the waveform detected when electrophoresis was performed without a short-pass filter and the Raman luminance obtained.
FIG. 8b is a characteristic diagram showing the waveform detected when electrophoresis was performed using a short-pass filter and the Raman luminance obtained.
Figure 8:
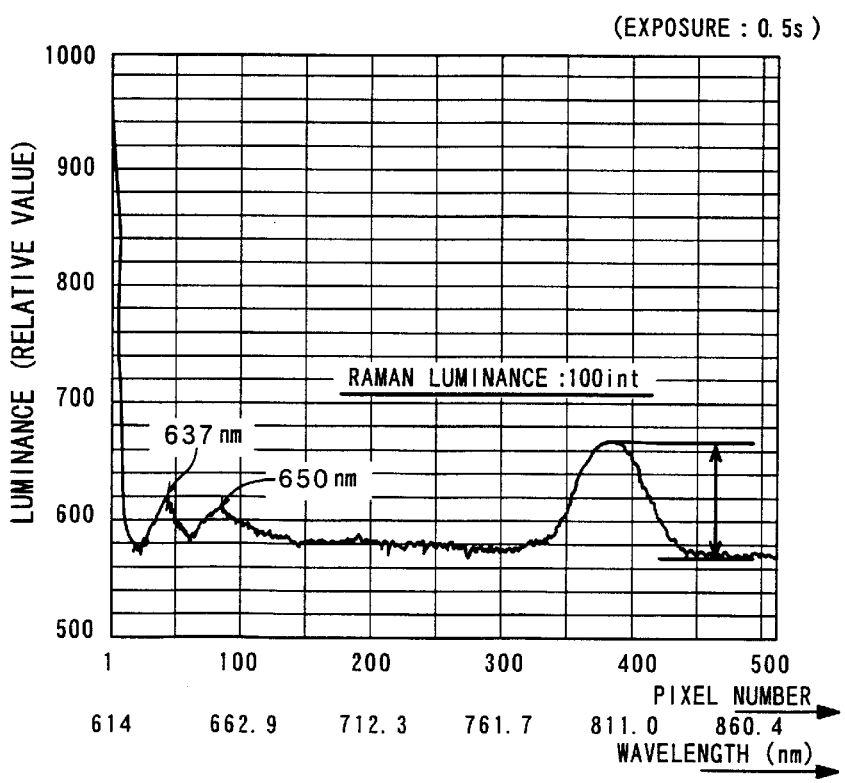

The effectiveness of using the short-pass filter 2 is apparent by comparing FIGS. 8a and 8b. FIG. 8a is a characteristic diagram showing the waveform detected when electrophoresis was performed without using the short-pass filter 2 and the Raman luminance obtained. Obviously, a side band from LD was detected at a wavelength of about 650 nm and fluorescence having the same or similar wavelengths could not be separated; what is more, the Raman luminance at the peak of about 800 nm was as weak as about 40 int. However, when the short-pass filter 2 was used in electrophoresis (see FIG. 8b), the inherent exciting light having a wavelength of 637 nm could be sharply separated from the fluorescence having a wavelength of 650 nm; what is more, the Raman luminance at the peak of about 800 nm increased to 100 int. One can therefore understand that the short-pass filter 2 is capable of increasing the Raman luminance by a factor of about 2.5. FIG. 8b shows that exciting light having a wavelength of 637 nm was also detected. This is because part of the exciting light having the wavelength of 637 nm passed through the long-pass filter 9 to be received by the CCD sensor as stray light. However, this stray light will cause no adverse effects on the result of measurement since it can be sharply distinguished from the fluorescence that need be detected at 650 nm.

Figure 9:
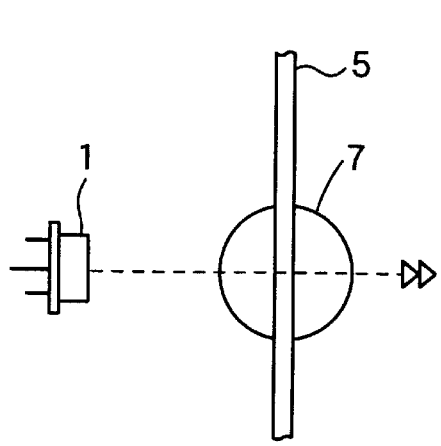
FIG. 9a is a schematic representation of laser light that is launched horizontally as in the prior art.
FIG. 9b is a schematic representation of laser light that is launched at an incident angle (θ) of 0°<θ<90° according to the invention.
Figure 9:
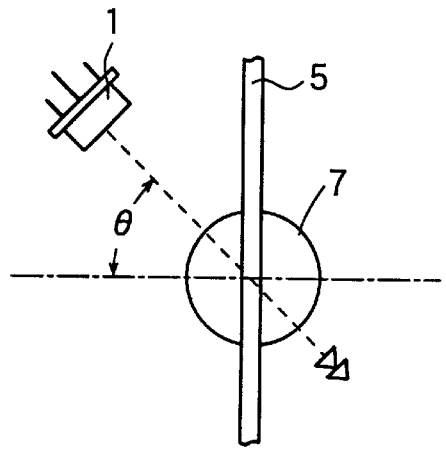

If a single capillary of the type shown in FIGS. 1 and 5 is used as the gel electrophoretic means 5, laser light is preferably incident on the capillary 5 at an angle with it rather than horizontally, because this contributes to reduce the scattering of the laser light incident on the capillary. As shown in FIG. 9a, laser light is conventionally admitted horizontal to the light-receiving plane of a fluorescence receiving element such as the first lens 7 (in other words, perpendicular to the capillary 5). This is not the case of the present invention which is shown in FIG. 9b; the laser light is admitted at a certain incident angle θ with the normal to the capillary 5 and this is effective in reducing the occurrence of scattered light. Typically, 0°<θ<90°, and preferably, 30°≦θ≦60°. Most preferably, θ=45°.

Figure 10:
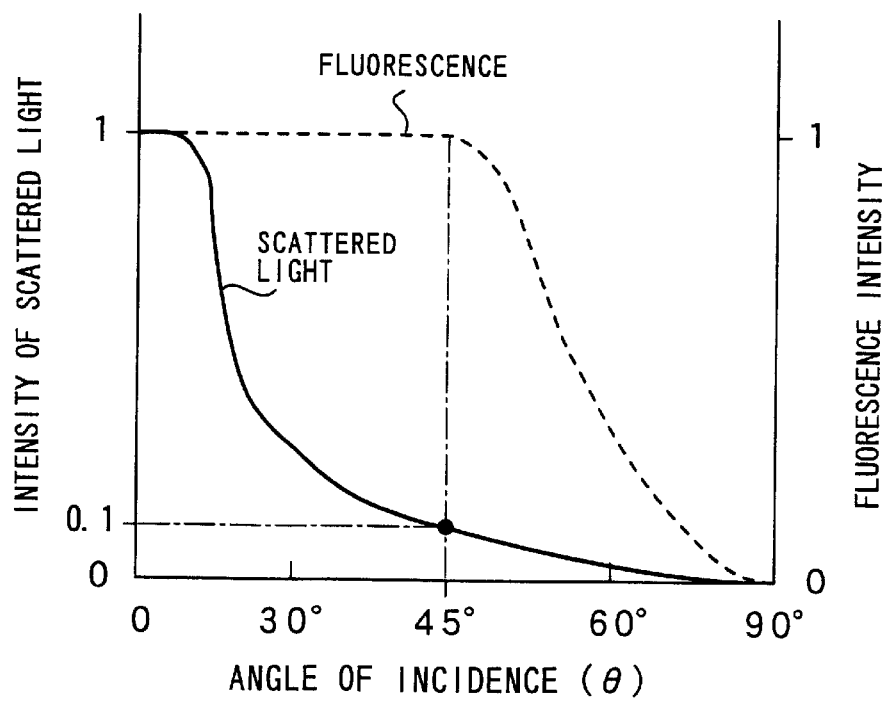
FIG. 10 is a characteristic diagram showing how the intensities of scattered light and fluorescence vary at incident angles of 0°<θ<90° according to the invention.
Figure 11:
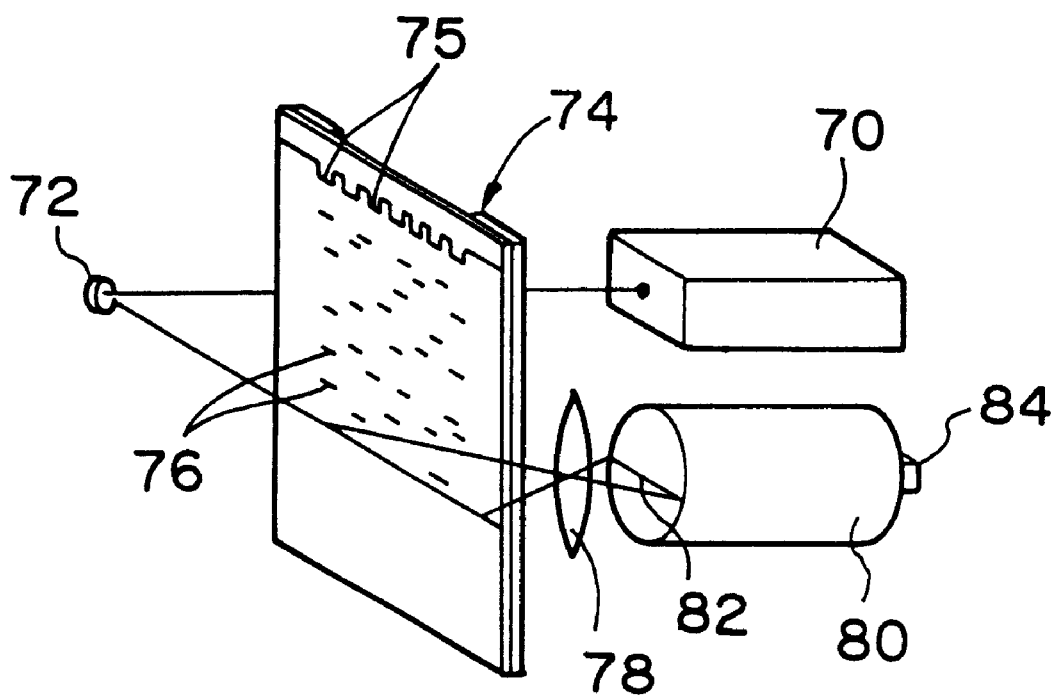
FIG. 11 shows schematically the layout of the DNA base sequencer disclosed in Japanese Laid-Open Patent Application (kokai) No. 21556/1988.

FIG. 10 is a characteristic diagram showing the variations in the intensities of scattered light and fluorescence as detected when the incident angle of laser light was varied from 0 to 90 degrees. The intensity of the scattered light (indicated by the solid line) was maximal when the laser light was admitted horizontally and it gradually decreased as the angle of incidence approached 90 degrees, at which it was minimal. The fluorescence intensity was virtually constant as long as the angle of incidence was between 0 and 45 degrees. In excess of 45 degrees, the fluorescence intensity started to decrease and it became almost zero at 90 degrees. At an incident angle of 45 degrees, the intensity of the scattered light was one tenth of the value obtained by horizontal incidence.

As described on the foregoing pages, a long-pass filter is used in the DNA base sequencer of the invention to reject the exciting light from LD that is contained in the fluorescence emitted from a sample of fluorophore-labeled DNA fragments and part of the exciting light that escaped the long-pass filter is received by a CCD sensor as stray light. The peak wavelength of the stray light provides a "departure" from the wavelength setting of the exciting light; the "departure" can be compensated by controlling the direction of the current to be flowed through a LD cooling Peltier device. If a forward current is applied, the Peltier device cools the LD; if a reverse current is applied, the LD is heated. By changing the direction of the current being applied to the Peltier device, its function can be changed from heating to cooling or vice versa. In this way, the wavelength of the exciting light can be maintained at the desired setting.

If a short-pass filter is provided between LD and the electrophoretic means, only that portion of the exciting laser light from the LD which has the desired wavelength of 637 nm can be transmitted while longer wavelengths are rejected.

If desired, the angle of incidence θ at which the exciting laser light emitted from the LD is admitted into the electrophoretic means in capillary form may be increased from the conventional zero degrees (horizontal incidence) to fall within the range of 0°<θ<90°, preferably 30°≦θ≦60°. Most preferably, θ=45° and the effect of scattered light can be reduced to about one tenth of the value obtained by horizontal incidence.

What is claimed is:

1. In a DNA base sequencer comprising a gel electrophoretic means having tracks for electrophoresing fluorophore-labelled DNA fragments, a laser diode as a light source for illuminating said tracks with exciting laser light and a CCD sensor for detecting the fluorescence emitted from the illuminated DNA fragments, the improvement wherein said laser diode has a control unit comprising a Peltier device for controlling the temperature of the laser diode, a Peltier device temperature setting generating means having a processor and a memory, and a temperature control circuit that generates a drive current to the Peltier device for controlling its temperature, and wherein said CCD sensor receives part of the exciting light from the laser diode as stray light and detects its wavelength and said Peltier device temperature setting generating means is such that, in accordance with the wavelength of stray light as detected periodically with said CCD sensor according to the program stored in said memory, calculates a corrective value that adjusts the detected wavelength of stray light to the desired wavelength of exciting light that corresponds to the desired temperature setting and an appropriate temperature setting signal is generated on the basis of said corrective value and said desired temperature setting and sent to the Peltier device temperature control circuit.

2. The DNA base sequencer according to claim 1, which further includes a long-pass filter provided between the gel electrophoretic means and the CCD sensor and wherein said stray light is part of the laser light from the laser diode that was transmitted through said long-pass filter.

3. The DNA base sequencer according to claim 2, which further includes a short-pass filter provided between said laser diode and said gel electrophoretic means on their optical axis.

4. The DNA base sequencer according to claim 2, wherein said gel electrophoretic means is a single hollow capillary, a first lens is provided ahead of said long-pass filter, a second lens is provided behind said long-pass filter, the fluorescence and stray light that were transmitted through said second lens pass through a slit in a plate and are reflected by a reflector mirror to be incident on a grating, and the fluorescence and stray light reflected by the grating are received by the CCD sensor.

5. The DNA base sequencer according to claim 1, which further includes a short-pass filter provided between said laser diode and said gel electrophoretic means on their optical axis.

6. The DNA base sequencer according to claim 5, which further includes a condenser lens provided between said laser diode and said short-pass filter on their optical axis.

7. The DNA base sequencer according to claim 6, wherein said gel electrophoretic means is a single hollow capillary, a first lens is provided ahead of said short-pass filter, a second lens is provided behind said short-pass filter, the fluorescence and stray light that were transmitted through said second lens pass through a slit in a plate and are reflected by a reflector mirror to be incident on a grating, and the fluorescence and stray light reflected by the grating are received by the CCD sensor.

8. The DNA base sequencer according to claim 5, wherein said gel electrophoretic means is a single hollow capillary, a first lens is provided ahead of said short-pass filter, a second lens is provided behind said short-pass filter, the fluorescence and stray light that were transmitted through said second lens pass through a slit in a plate and are reflected by a reflector mirror to be incident on a grating, and the fluorescence and stray light reflected by the grating are received by the CCD sensor.

9. The DNA base sequencer according to claim 2, wherein said gel electrophoretic means is a single hollow capillary, a first lens is provided ahead of said long-pass filter, a second lens is provided behind said long-pass filter, the fluorescence and stray light that were transmitted through said second lens pass through a slit in a plate and are reflected by a reflector mirror to be incident on a grating, and the fluorescence and stray light reflected by the grating are received by the CCD sensor.

10. The DNA base sequencer according to claim 9, wherein the laser diode is provided in such a position that laser light is launched at an incident angle greater than zero degrees but smaller than 90 degrees with respect to the normal to the capillary.

11. The DNA base sequencer according to claim 10, wherein the laser diode is provided in such a position that laser light is launched at an incident angle between 30 and 60 degrees with respect to the normal to the capillary.

12. The DNA base sequencer according to claim 11, wherein the laser diode is provided in such a position that laser light is launched at an incident angle of 45 degrees with respect to the normal to the capillary.

* * * * *